(12) United States Patent
Holmgren et al.

(10) Patent No.: US 6,365,163 B1
(45) Date of Patent: Apr. 2, 2002

(54) IMMUNOLOGICAL TOLERANCE-INDUCING AGENT

(75) Inventors: Jan Holmgren, Korvettgatan (SE); Cecil Czerkinsky, Le Florence (FR)

(73) Assignee: Duotol, Vasta Frolunda (SE)

( * ) Notice: Subject to any disclaimer, the term of this patent is extended or adjusted under 35 U.S.C. 154(b) by 0 days.

(21) Appl. No.: 09/625,003

(22) Filed: Jul. 25, 2000

Related U.S. Application Data

(60) Division of application No. 08/883,817, filed on Jun. 27, 1997, which is a continuation of application No. 08/420,981, filed on Apr. 10, 1995, now abandoned, which is a continuation-in-part of application No. 08/184,458, filed on Jan. 19, 1994, now Pat. No. 5,681,571, which is a continuation-in-part of application No. 08/160,106, filed on Nov. 30, 1993, now abandoned.

(30) Foreign Application Priority Data

Oct. 8, 1993 (SE) ............................................... 9303301

(51) Int. Cl.$^7$ ...................... A61K 39/02; A61K 39/108; A61K 39/106

(52) U.S. Cl. ................................ 424/236.1; 424/241.1; 424/275.1; 424/282.1; 424/810; 514/885; 530/868

(58) Field of Search ........................... 424/275.1, 241.1, 424/236.1, 282.1, 810; 514/885; 530/868

*Primary Examiner*—Rodney P Swartz
(74) *Attorney, Agent, or Firm*—Darby & Darby

(57) ABSTRACT

An agent comprising a mucosa-binding molecule linked to a specific microbial antigen is disclosed. Further, a method of inducing immnunological tolerance in an individual against a specific microbial antigen, including hapten, which causes an unwanted immune response in said individual, comprising administration by a mucosal route of an immunologically effective amount of an immunological tolerance-inducing agent of the invention to said individual, is described.

16 Claims, No Drawings

IMMUNOLOGICAL TOLERANCE-INDUCING AGENT

This application is a divisional of U.S. patent application Ser. No.08/883,817, filed Jun. 27, 1997, which is a continuation of Ser. No. 08/420,981 filed Apr. 10, 1995, now abandoned, which was a continuation-in-part of application Ser. No.08/184,458, filed Jan. 19, 1994, which issued as U.S. Pat. No. 5,681,571, on Oct. 28, 1997, which was a continuation-in-part of application Ser. No. 08/160,106, filed Nov. 30, 1993 now abandoned.

FIELD OF THE INVENTION

The present invention relates to inflammatory reactions caused by certain infectious microorganisms. Specifically, it relates to an agent comprising a mucosa-binding molecule linked to a specific antigen derived from a microorganism, which is useful in inducing systemic immunological tolerance to the specific antigen and thus preventing or treating deleterious inflammatory reactions caused by the microorganism.

BACKGROUND OF THE INVENTION

Introduction of a foreign substance, herein referred to as an antigen (Ag), including a hapten, by injection into a vertebrate organism can result in the induction of an immune response. Typically, an immune response involves the production of specific antibodies (products of B lymphocytes) capable of interacting with the antigen and/or the development of effector T lymphocytes and the production of soluble mediators, termed lymnphokines, at the site of encounter with the antigen. Antibodies and T lymphocytes play essential roles in protecting against a hostile antigen; under certain circumstances, however, they also participate in injurious processes in response to an antigen that lead to destruction of host tissues. For example, the local reaction of antibodies and/or T lymphocytes with an antigen derived from an infectious microorganism at certain anatomical sites can cause extensive tissue damage. This is the case in chronic inflammatory reactions that develop as a result of ineffective elimination of foreign materials, as in certain infections (e.g. tuberculosis, schistosomiasis, and infections caused by Chlamydia, *Helicobacter pylori, Pneumocystis carinii,* etc.) where immunoproliferative reactions develop at the site(s) of microbial colonization.

To develop vaccines effective against infectious microorganisms that cause destructive immunological reactions, it is desirable, on the one hand, to specifically prevent or reduce the rate of entry of the microorganisms into internal organs (or the uptake of potentially harmful components, such as toxins derived from these microorganisms), and, on the other hand, to specifically suppress (or decrease to an acceptable level) the intensity of deleterious immune processes without affecting the remainder of the immune system.

The most frequent portals of entry of common microbes are the mucosal surfaces covering the digestive tract, the respiratory tract, the urogenital tract, the eye conjunctiva, the inner ear, and the ducts of exocrine glands, which collectively represent the largest (400 $m^2$) organ system in upper vertebrates. Endowed with powerful mechanical and physicochemical cleansing mechanisms, these surfaces are further protected by a specialized immune system that guards them against potential insults from the environment. This system, termed "mucosa-associated lymphoid tissue" (MALT), is the largest mammalian lymphoid organ system, and represents a well-known example of a compartmentalized immunological system. Through the compartmentalization of its afferent and efferent limbs, MALT functions essentially independently from the systemic immune apparatus, the latter system comprising peripheral lymphoid organs such as the blood, the bone marrow, the spleen, peripheral lymph nodes, and the thymus. This notion explains why systemic injection of immunogens is relatively ineffective at inducing an immune response in mucosal tissues.

The predominant component of the immune response expressed by MALT is the elaboration of secretory immunoglobulin A (SIgA), the predominant Ig class in human external secretions and one that provides specific immune protection for mucosal tissues. SIgA antibodies provide "immune exclusion" of bacteria and viruses, bacterial toxins, and other potentially harmful molecules, and have also been reported to neutralize certain viruses directly, to mediate antibody-dependent cell-mediated cytotoxicity (in cooperation with macrophages, lymphocytes and eosinophils), and to interfere with the utilization of growth factors for bacterial pathogens in the mucosal environment.

In contrast to the systemic immune apparatus, which is in a sterile compartment and responds vigorously to most invaders, the mucosal immune system guards organs that are replete with foreign matter including microorganisms. It follows that, upon encounter with a given antigen, the mucosal immune system must select appropriate effector mechanisms and regulate the intensity of its response so as to avoid bystander tissue damage and depletion of the immune response capacity.

In addition to inducing local SIgA antibody responses, ingestion or inhalation of antigens (mucosal route) may also result in the development of a state of peripheral immunological tolerance. Tolerance is characterized by a lack of immune responses in non-mucosal tissues when an antigen initially encountered in the digestive tract mucosa or the respiratory mucosa is reintroduced in the organism by a non-mucosal route such as by parenteral injection. Mucosal administration of antigens is in fact a long-recognized method of inducing immunological tolerance (Wells, H., *J. Infect. Dis.* 9:147, 1911). The phenomenon, often referred to as "oral tolerance" because it was initially documented by the effect of oral administration of antigen, is characterized by the fact that animals fed or having inhaled an antigen become refractory or have diminished capability to develop a systemic immune response when re-exposed to said antigen introduced by the systemic route, e.g., by injection. In broad terms, application of an antigen onto a mucosal membrane or into a mucosal tissue, be it the intestine, the lung, the mouth, the genital tract, the nose, or the eye, can induce the phenomenon of systemic immunological tolerance. By contrast, introduction of an antigen into a non-mucosal tissue, such as, for example, by a subcutaneous or intravenous route (referred to as systemic immunization) often results in an affirmative systemic immune response.

The phenomenon of "oral tolerance" is highly specific for the antigen that was introduced by the mucosal route. That is, hypo-responsiveness can only be documented subsequent to injection of the same antigen used to tolerize, but not after injection of a structurally unrelated antigen that had not been encountered previously at mucosal sites.

The specificity of oral tolerance for the initially ingested or inhaled antigen, and the lack of effect on the development of systemic immune responses against other antigens, makes it an increasingly attractive strategy for preventing and treating illnesses associated with or resulting from the development of untoward and/or exaggerated immunological reactions against specific antigens encountered in non-mucosal tissues.

The phenomenon of mucosally induced systemic tolerance may involve all types of immune responses known to be inducible by the systemic introduction of antigen, such as the production of specific antibodies and the development of cell-mediated immune responses to the antigen. Mucosally induced immunological tolerance has therefore been proposed as a strategy to prevent or to reduce the intensity of allergic reactions to chemical drugs (Chase, M. W., *Proc. Soc. Exp. Biol.* 61:257–259, 1946). It has also been possible in experimental animals and in humans to prevent or decrease the intensity of immune reactions to systemically introduced soluble protein antigens and to particulate antigens such as red cells by the oral administration of red cells (Thomas H. C. et al., *Immunology* 27:631–639, 1974; Mattingly, J. et al., *J. Immunol.* 121:1878, 1978; Bierme, S. J. et al., *Lancet,* 1:605–606, 1979). The phenomenon of mucosally induced systemic tolerance can be utilized to reduce or suppress immune responses not only against foreign antigens but also against self antigens, i.e., components derived from host tissues.

It has also been shown that the enteric administration of schistosome eggs in mice prevented the development or decreased the intensity of hepatic and intestinal granulomatous reactions, which are chronic T cell-mediated inflammatory immune reactions that develop around schistosome eggs during infestation by the parasite Schistosoma (Weinstock, J V et al., *J. Immunol.* 135:560–563, 1985). Other microorganisms that cause inflammatory (delayed-type hypersensitivity) reactions include *Mycobacterium tuberculosis, Mycobacterium avium, Listeria monocytogenes, Brucella abortus, Chlamydia trachomatis,* Mycoplasma sp., *Porphyromonas (Bacteroides) gingivalis, Helicobacter pylori,* Salmonella sp., Shigella sp., Yersinia sp. Cryptosporidium sp., Borrelia sp., *Pneumocystis carinii, Candida albicans, Histoplasma capsulatum, Cryptococcus neoformans,* Leishmania sp., Plasmodium, Trypanosoma, paramyxoviruses such as respiratory syncytial virus, adenovirus, poliovirus, hepatitis virus, vaccinia and other poxviruses, rhinovirus, herpes simplex virus, variola, and measles virus.

Although the above examples indicate that mucosal administration offoreign antigens offers a convenient way to induce specific immunologic tolerance, its applicability to large scale therapy in human and veterinary medicine remains limited by practical problems. For example, for broad applicability, mucosally-induced immunological tolerance must also be effective in patients in whom the disease process has already established itself and/or in whom potentially tissue-damaging immune cells already exist. This is especially important for patients suffering from (or prone to) a chronic inflammatory reaction to a persistent microorganism. Current protocols for mucosally induced tolerance have had limited success in suppressing the expression of an already established state of systemic immunological sensitization (Hansson, D. G. et al., *J. Immunol.* 122:2261, 1979).

Most importantly, and by analogy with mucosal vaccines (i.e., preparations used to induce immune responses to infectious pathogens), induction of systemic immunological tolerance by mucosal application of most antigens requires considerable amounts of the tolerogen/antigen, and the tolerance is of relatively short duration, unless the tolerogen/antigen is administered repeatedly over long periods oftime. A likely explanation is that most antigens are extensively degraded before entering a mucosal tissue and/or are absorbed in insufficient quantities. It has thus been widely assumed that only molecules with known mucosa-binding properties can induce local and systemic immune responses when administered by a mucosal route, such as the oral route, without inducing systenmic immunological tolerance (de Aizpurua, H. J. et al., *J. Exp. Med.* 167:440–451, 1988). Examples of mucosa-binding molecules are listed in Table I below; see also reviews such as Mirelman D., *Microbial Lectins and Agglutinins, Properties* and *Biological Activity,* pp. 84–110, Wiley, New York, 1986). A notable example is cholera toxin, one of the most potent mucosal immunogens known so far (Elson, C. O. et al., *J. Immunol.* 132:2736, 1984), which can also prevent induction of systemic immunological tolerance to an antigen when orally administered simultaneously with the unrelated antigen (Elson, C. O. et al., *J. Immunol.* 133:2892, 1984).

Based on these observations, mucosal administration of antigens coupled to mucosa-binding molecules such as cholera toxin (or its mucosa-binding fragment, cholera toxin B subunit), has been proposed as a strategy to induce local and systemic immune responses rather than systemic tolerance (McKenzie, S. J. et al., *J. Immunol.* 133:1818–1824, 1984; Nedrud, J. G. et al., *J. Immunol.* 139:3484–3492, 1987; Czerkinsky, C. et al., *Infect. Immun.* 57:1072–1077, 1989; de Aizpurua, H. J. et al., *J. Exp. Med.* 167:440–451, 1988; Lehner, T. et al., *Science* 258(5036):1365–1369, 1992).

SUMMARY OF TH EINVENTION

The present invention provides an immunological tolerance-inducing agent comprising a mucosa-binding molecule linked to a specific antigen derived from an infectious microorganism. The infectious microorganism may be any microorganism, including bacteria, viruses, fungi, helminths, and protozoa, that causes an unwanted immune response, particularly delayed-type hypersensitivity (DTH), in a host following infection. The antigens used for inducing tolerance, called tolerogens, may comprise components of the microorganisms that contain DTH epitopes, i.e., structural determinants that stimulate a DTH response.

The mucosa-binding molecules used to form the tolerance-inducing agent may be derived from viral attachment proteins, lectins, and bacterial fimbriae, although preferred mucosa-binding molecules comprise pure cholera toxin B subunit, pure *E. coli* heat labile enterotoxin B subunit, or mucosa-binding fragments thereof.

The mucosa-binding molecules and the tolerogens may be linked to each other directly or indirectly, and the linkage may be covalent or non-covalent. For example, the tolerogen may be chemically cross-linked to a mucosa-binding molecule, or may be genetically fused to amino acid sequences comprising the mucosa-binding molecule. Alternatively, the tolerogen may be linked to the mucosa-binding molecule via a spacer molecule, such as a bifinctional antibody.

In another aspect, the present invention encompasses methods for inducing in an individual tolerance to a specific antigen derived from an infectious microorganism. The method is carried out by administering to the individual the tolerance-inducing agent as above, in an amount effective to induce tolerance.

DETAILED DESCRIPTION OF THE INVENTION

All patents, patent applications, and references referred to in this specification are hereby incorporated by reference in their entirety. In the case of inconsistencies, the present disclosure, including definitions, will prevail.

The present invention is directed towards methods and compositions for inducing immunological tolerance to antigens derived from infectious microorganisms, in particular, antigens that cause an unwanted immune response in a host following infection with the microorganism. The compositions comprise a mucosa-binding molecule linked to a specific microbial antigen. Contrary to established opinion that mucosal administration of antigens coupled to mucosa-binding molecules induces local and systemic immune responses without inducing tolerance, the present inventors have unexpectedly found that mucosal administration of antigens coupled to mucosa-binding molecules according to the present invention induces systemic immunological tolerance to the antigens.

As used herein, "immunological tolerance" refers to a reduction in immunological reactivity of a host towards a specific antigen or antigens. The antigens comprise immune determninants that, in the absence of tolerance, cause an unwanted immune response, such as, for example, acute or chronic inflammation caused by delayed-type hypersensitivity (DTH). DTH is characterized by an immune response at the site of exposure to antigen, which comprises an initial infiltration of neutrophils followed by accumulation of T lymphocytes and blood monocytes, deposition of fibrin, and induration. "Antigens" as used herein include haptens, which are compounds that do not stimulate a primary immune response but may trigger a DTH response in a pre-sensitized animal.

An antigen that, when incorporated into a tolerance-inducing agent according to the present invention, promotes the development of tolerance, e,g., the prevention or reversal of DTH, is referred to herein as a "tolerogen". Tolerogens typically comprise "DTH epitopes", which are the particular structural determinants that, in the absence of tolerance, stimulate a DTH response. DTH epitopes may be distinct from "IgA epitopes", which are structural determinants that stimulate the local production of antigen-specific IgA by B lymphocytes in the mucosa. Preferably, tolerogens used in practicing the present invention comprise DTH epitopes and not IgA epitopes.

The present invention encompasses microbial antigens that cause an unwanted immune response in an individual subsequent to infection of the individual by the microbe. The antigens may comprise any component ofthe microorganism that, for example, carries DTH epitopes and excludes IgA epitopes. The antigens may comprise without limitation proteins, peptides, carbohydrates, lipids, nucleic acids, and combinations thereof. Preferably, the antigens comprise peptides or proteins.

The microorganisms from which the antigens are derived may be any microorganism that causes an unwanted immune reaction, e.g., DTH, following infection. The microorganism may be a bacterium, a virus, a fungus, or a parasite such as a helminth or a protozoan. Examples of such microorganisms include without limitation *Mycobacterium tuberculosis, Mycobacterium avium, Listeria monocytogenes, Brucella abortus, Chlamydia trachomatis,* Mycoplasma sp., *Porphyromonas* (*Bacteroides*) *gingivalis, Helicobacter pylori,* Salmonella sp., Shigella sp., Yersinia sp. Cryptosporidium sp., Borrelia sp., *Pneumocystis carinii, Candida albicans, Histoplasma capsulatum, Cryptococcus neoformans,* Leishmania sp., Plasmodium, Trypanosoma, paramnyxoviruses (such as respiratory syncytial virus), adenovirus, poliovirus, hepatitis virus, vaccinia and other poxviruses, rhinovirus, herpes simplex virus, variola, and measles virus.

Examples of specific microbial antigens that cause an unwanted immune response in an individual, and which may comprise the specific tolerogen in the immunological tolerance-inducing agent of the present invention, include without limitation: 1) Bacterial toxins or fragments thereof. For example, septicemia-like toxic shock syndrome is induced by systemic exposure to endotoxins (a group of lipopolysaccharides produced by gram negative bacteria) or to certain exotoxins such as staphylococcal enterotoxins; 2) Heat-shock proteins or fragments thereof. As used herein, "heat shock protein" encompasses members of different families of stress proteins (some of which are synthesized constitutively), including without limitation, hsp 60s, hsp 70s, and hsp90s. For example, mycobacterial hsp 55 causes a granulomatous DTH reaction directed against mycobacteria that develops in the lung during tuberculosis. Similarly, chlamydial cells may secrete a 57–60 kDa heat shock protein (hsp), which elicits a DTH reaction in genital and ocular tissues leading to pelvic inflammation and trachoma, respectively; 3) A surface component of a bacteria, virus, fungus, or other microbe, or fragments thereof. For example, the F protein of respiratory syncytial virus comprises a prominent epitope that triggers DTH reactions in infected lung tissue.

It will be understood by those skilled in the art that other antigens suitable for incorporation in the tolerance-inducing agents of the present invention can be purified from their respective microorganisms using well-known methods. For example, whole killed microorganisms can be disrupted and fractionated into component subcellular fractions, using standard chromatographic or electrophoretic methods. The fractions can then be assayed for the presence of DTH epitopes in the following manner: T-cells reactive with the microorganism are obtained from the blood of infected or convalescent patients, or from the spleen or lymph nodes of experimentally infected animals. The T cells are reacted in cell culture with subcellular fractions (or with partially purified or purified components derived therefrom), after which T-cell proliferation is quantified using standard techniques such as, for example, incorporation of $^3$H-thymidine into DNA. Alternatively, the stimulation of production of cytokines such as, for example, interleukin-2, can be measured after exposure of the T cell population to the cell fractions or components. A DTH epitope derived from the microorganism is identified by the stimulation of $^3$H-thymidine incorporation or of interleukin-2 production in the T-cell culture.

Another method for identifiing microbial components that contain DTH epitopes is to systemically immunize an experimental animal such as, for example, a mouse, with the microorganism (in an emulsion with an adjuvant such as Freund's) via a subcutaneous or intraabdominal route. After maintaining the mouse for a sufficient time to induce a systemic immune reaction, the potential DTH epitope-containing fraction or component is then injected into the footpad of the animal, and the appearance of a DTH reaction is monitored.

According to the present invention, antigens comprising a DTH epitope are linked to a mucosa-binding molecule to form an immunological tolerance-inducing agent. Mucosa-binding molecules useful in practicing the present invention include without limitation mucosa-binding subunits or domains of bacterial toxins, bacterial fimbriae, viral attachment proteins, and lectins. Non-limiting examples of these types of mucosa-binding molecules are listed in Table 1.

TABLE 1

Examples of classes and types of mucosa-binding molecules

A. Bacterial toxins and their binding subunits or fragments
e.g., Cholera toxin, cholera B subunit;
　　　Escherichia coli heat-labile enterotoxin (LT), LT B subunit;
　　　Bordetella pertussis toxin, subunits S2, S3, S4 and/or S5;
　　　Diphtheria toxin (DT), DT B fragment;
　　　Shiga toxin, Shiga-like toxins and B subunits
B. Bacterial fimbriae
e.g., Escherichia coli; K88, K99, 987P, F41, CFA/I, CFA/II, (CS1, CS2 and/or CS3), CFA/IV (CS4, CS5 and/or CS6), P fimbriae etc.;
　　　Vibrio cholerae toxin-coregulated pilus (TCP), mannose-sensitive hemagglutinin (MSHA), fucose-sensitive hemagglutinin (FSHA) etc.;
　　　Bordetella pertussis filamentous hemagglutinin;
C. Viral attachment proteins
e.g. Influenza and Sendai virus hemagglutinins
　　　RIV gp120;
D. Animal lectins and lectin-like molecules
e.g. Immunoglobulins;
　　　Calcium-dependant (C-type) lectins;
　　　Soluble lactose-binding (S-type) lectins;
　　　Selectins;
　　　Collectins;
　　　Helix pomatia hemagglutinin
E. Plant lectins
e.g. Concanavalin A
　　　wheat-germ agglutinin
　　　Phytohemagglutinin
　　　Abrin
　　　Ricin Preferred mucosa-binding molecules are mucosa-binding subunits or domains of bacterial toxins such as cholera toxin or E. coli heat-labile enterotoxin; most preferred is pure cholera toxin B subunit (CTB). "Pure" as used in this context means that the cholera toxin B subunit is essentially free of detectable contamination by active cholera toxin, which comprises a cholera toxin A subunit (CTA) in combination with CTB. An "active" cholera toxin molecule as used herein denotes one that exhibits ADP-ribosylating activity. Functional purity of cholera toxin B subunit for use in the present invention can be achieved by expressing the gene encoding cholera toxin B subunit in a bacterial cell (such as, for example, E. coli or V. cholerae) in the absence of a gene encoding the cholera toxin A subunit. Methods for large-scale expression of pure cholera toxin B subunit are disclosed in, for example, U.S. Pat. No. 5,268,276. As shown in Example 6 below, the present inventors have found that the presence of even small amounts of contaminating cholera toxin A subunit can abrogate the tolerance induced by the compositions of the present invention. The present invention also encompasses mucosa-binding fragments of, e.g., CTB or LTB.

In practicing the present invention, the tolerogen and the mucosa-binding molecule may be linked to each other directly or indirectly. In both cases, the linkages may be covalent or non-covalent (e.g., via electrostatic and/or hydrophobic interactions).

In one embodiment, direct linkage between the tolerogen and mucosa-binding molecule is achieved by chemically cross-linking the tolerogen and the mucosa-binding moiety. It will be understood that any suitable method may be used to cross-link the components, as long as the final cross-linked product retains the ability to induce tolerance to the specific antigen employed. Suitable chemical cross-linking procedures are well-known in the art; see, for example, Carlsson J. et al., Biochem. J. 173:723–737, 1978; Cumber, J. A. et al. Methods in Enzymology 112:207–224, 1985; Walden, P. et al., J. Mol. Cell Immunol. 2:191–197, 1986; Gordon, R. D. et al., Proc. Natl. Acad. Sci. (USA) 84:308–312,1987; Avrameas, S. etal., Immuno-chemistry 6:53,1969; Joseph, K. C. et al., Proc. Natl. Acad. Sci. USA 75:2815–2819, 1978; Middlebrook, J. L. et al., Academic Press, New York, pp. 311–350, 1981).

In another embodiment, direct linkage is achieved by the design and expression of a recombinant chimeric gene encoding a fusion protein that comprises the tolerogen, or a fragment thereof containing a DTH epitope, which is fused to a mucosa-binding peptide or polypeptide (Sanchez et al., FEBS Letts. 241:110, 1988). The chimeric gene is then expressed in a suitable expression system, including without limitation bacteria, yeast, insect cells, or mammalian cells, and the hybrid protein gene product isolated therefrom.

Indirect linkage between the tolerogen and the mucosa-binding molecule may be achieved using a spacer molecule. Preferably, the spacer molecule has an affinity for either the tolerogen, the mucosa-binding molecule, or both. In one embodiment, the spacer comprises an antibody, preferably a bifunctional antibody that recognizes both the tolerogen and the mucosa-binding molecule. In another embodiment, the spacer molecule is derived from the cholera toxin-binding structure of the GM1 ganglioside, galactosyl-N-acetyl-galactosaminyl-(sialyl)-galactosylglucosylceramide. In these cases, the linkages are formed by high-affinity binding between the spacer and the other components. The only requirement is that the tolerogen and mucosa-binding molecule both remain linked to each other via the spacer during mucosal administration. In the case of spacer molecules that do not have specific affinity for either tolerogen or mucosa-binding molecule, chemical cross-linking methods may be used as described above to form covalent linkages between the components. In another embodiment, an indirect linkage may be achieved by encapsulating the tolerogen within a protective vehicle such as a liposome (or equivalent biodegradable vesicle) or a microcapsule, on the surface of which the mucosa-binding molecule is arrayed. In this type of presentation form, the tolerogen may be free within the lumenal space of the vesicle or microcapsule, or may be bound to other components. The only requirement is that the tolerogen and the mucosa-binding molecule remain in close enough proximity during mucosal administration such that the tolerogen is effectively delivered to the mucosa.

In yet another embodiment, the tolerance inducing agent comprises a nucleic acid sequence encoding the tolerogen, which is then chemically coupled to the mucosa-binding molecule and administered by the mucosal route. "Nucleic acid" as used herein denotes DNA, both single- and double-stranded, with a sugar backbone of deoxyribose, methylphosphonate, or phosphorothioate; "protein nucleic acid: (PNA), which comprises nucleotides bound to an amino acid backbone; and all forms of RNA. This method requires cells in the host mucosal tissues to transcribe and translate the corresponding gene into a mature peptide or protein (Rohrbaugh, M. L. et al, *N. Y. Acad. Sci.* 685:697–712, 1993; Nabel, G. J. et al., *Trends in Biotechnology* Vol. 11, No. 5, pp. 211–215, 1993; Robinson, H. L. et al., *Vaccine* 11:957–960, 1993; Martinon, F. et al., *Eur. J. Immunol.* 23:1719–1722, 1993).

The present invention is also directed to a method of inducing in an individual immunological tolerance against a specific microbial antigen that causes an unwanted immune response, such as, for example, DTH. The method comprises administering to the individual by a mucosal route an immunological tolerance-inducing agent as described above.

The methods ofthe present invention can be practiced preventively or therapeutically. That is, the timing of administration relative to the time of exposure to microbial antigens is not limiting. For example, the tolerance inducing agent can be administered to individuals who have been deemed "at-risk" for developing immune-mediated tissue damage caused by tuberculosis, or to patients who have already exhibited clinical indication of tuberculosis. Similarly, women harboring chlamydia infections are often asymptomatic and thus the agent could be given preventively or after the infection has been diagnosed.

Examples of pathological syndromes to which the methods and compositions of the present invention may be applied include, without limitation, tuberculosis, chlamydial infections, schistosomiasis, leprosy, pneumocystis pneumonia, leishmaniasis, and infections by *Candida albicans, Plasmodium, Trypanosoma, Listeria monocytogenes, Brucella abortus,* mycoplasma sp., *Porphyromonas* (*Bacteroides*) *gingivalis, Helicobacter pylori,* Salmonella sp., Shigella sp., Yersinia sp., *Histoplasma capsulatum, Cryptococcus neoformans,* Cryptosporidium sp., Borellia sp., as well as by the following viruses: paramyxoviruses such as respiratory syncytial virus, adenovirus, poliovirus, hepatitis virus, vaccinia and other poxviruses, rhinovirus, herpes simplex virus, variola, and measles virus.

It is also contemplated that the present methods can be used to induce tolerance against live microorganisms (recombinant or native) used for delivery of vaccinal antigens. Examples include recombinant live bacteria, e.g., BCG, Salmonella, Shigella, Lactobacillus; and viruses, e.g., adenovirus, poliovirus, poxviruses, Semliki Forest Virus, and retroviruses.

Target tissues suitable for mucosal administration according to the present invention include without limitation the gastrointestinal tract (including the mouth and throat), the respiratory tract (including the nose), the eye, and the genital tract. Thus, tolerance-inducing agents or compositions are formulated into dosage unit forms for mucosal administration, such as for example, creams, ointments, lotions, powders, liquids, tablets, capsules, suppositories, sprays, or the like. Dosage unit forms can include, in addition, one or more pharmaceutically acceptable excipient (s), diluent(s), disintegrant(s), lubricant(s), plasticizer(s), colorant(s), dosage vehicle(s), absorption enhancer(s), stabilizer(s), bactericide(s), or the like. One or more immunologically active substances that enhance the tolerogenic activity of these formulations may also be included, e.g., cytokines such as interleukin-10 (IL-10), interleukin-4 (IL-4), and transforming growth factor-beta (TGF-â).

The tolerance-inducing agents are present in the dosage forms such that a single dosage unit contains between about 1 ig and about 10 mg of the agent, preferably between about 10 ig and about 1 mg. Each dosage unit may contain an amount of active agent effective to induce tolerance. Alternatively, the dosage unit form may include less than such an amount, if multiple dosage unit forms or multiple dosages are to be used to administer a total dosage of the active agent.

It will be understood that the administration regimen for prevention or treatment of an unwanted immune response caused by an infectious microorganism will depend upon the particular organism (and immune response), as well as on the dosage form used. Without wishing to be bound by theory, it is contemplated that effective dosages will be much lower than those employed with tolerogen alone. An administration regimen effective in preventing or treating a particular unwanted immune response can be determined by experimentation known in the art, such as by establishing a matrix of dosages and frequencies and comparing a group of experimental units or subjects to each point in the matrix. Specifically, blood is obtained from experimental subjects and lymphocytes are isolated therefrom. The lymphocytes are then exposed to antigen alone (i.e., in the absence of a mucosa-binding molecule), and T-lymphocyte proliferation is measured as described above (e.g., by incorporation of $^3$H-thymidine). The efficacy of the tolerization method is indicated by a lessening of lymphocyte proliferation in response to antigen relative to controls. Similarly, the efficacy of tolerization may be monitored by measuring the production of cytokines such as interleukin-2 (IL-2) by the lymphocytes in response to antigen. In this case, the less IL-2 produced, the more effective the induction of tolerance.

DESCRIPTION OF THE PREFERRED EMBODIMENTS

The present invention is exemplified by the use of cholera toxin B subunit (CTB) and *E. coli* heat-labile enterotoxin B subunit (LTB) as mucosa-binding molecules, and the use of sheep red blood cells (SRBC) and human gamma-globulins (HGG) as antigens/tolerogens. Though neither antigen is derived from a microorganism, these antigens are excellent models of particulate and soluble antigens, respectively. They are among the best characterized oral tolerogens with regard to both antibody formation and cell-mediated immune reactions, the latter reactions being typified by the classical delayed-type hypersensitivity (DTH) reaction.

The following experiments are provided for the purpose of illustrating the subject invention but in no way limit its scope.

Materials and Methods

Inbred Balb/c female mice were obtained from the Animal Care Facility of the Department of Medical Microbiology and Immunology, University of Göteborg, Sweden. Mice 6–8 weeks of age were used.

Purification of the Mucosa-binding Molecules CTB and LTB

Recombinant cholera toxin B subunit (CTB) was produced in a mutant strain of *Vibrio cholerae* deleted of the cholera toxin genes and transfected with a plasmid encoding the CTB subunit (Sanchez, J. et al., *Proc. Natl. Acad. Sci USA* 86:481–485, 1989). Recombinant B subunit of *Escherichia coli* heat-labile enterotoxin (LTB) was produced in a similar mutant strain of *Vibrio cholerae* deleted of the cholera toxin genes and transfected, in this case, with a plasmid encoding *E. coli* LTB (Hirst T. R., et al., *Proc. Natl. Acad. Sci. USA,* 81:7752–7756, 1984). In these expression systems, CTB and LTB are recovered from bacterial growth media as secreted proteins. Bacterial cultures were centrifuged at 8000 rpm for 20 min, and the supernatants were collected and adjusted to pH 4.5 with dilute HCl. After precipitation with hexametaphosphate (final concentration 2.5 g/l) for 2 hours at 23° C. followed by centrifugation at 8000 rpm, the pellets were resuspended in 0.1 M sodium phosphate buffer, pH 8.0, and were dialysed against 0.01 M phosphate-buffered saline, pH 7.2. The dialysate was then centrifuged at 15 000 rpm to remove residual insoluble material and the supernatant was further clarified by filtration through a 0.22 Fm filter (Millipore, Bedford, Mass.). Finally, CTB and LTB were purified by standard gel filtration chromatography through columns of Sephadex G-100 (Pharmacia, Sweden).

Purification of Human Gamma-globulins (HGG)

HGG was purified from pooled human sera by sequential precipitation with $(NH_4)_2SO_4$ (final concentration 40%), followed by gel filtration chromatography on a column of Sephacryl S-300 HR (Pharmacia, Sweden) previously equilibrated with phosphate-buffered saline (0.2 M sodium phosphate, NaCl 0.1 M, pH 8.5). The resulting HGG preparation was diluted to 15 mg/ml.

Preparation of CTB-conjugated Sheep Red Blood Cells (SRBC-CTB)

Sheep red blood cells (SRBC) were stored at 4° C. in Alsevier's solution until use. Immediately prior to use, SRBC were washed 3 times with phosphate-buffered saline (PBS) (0.01 M sodium phosphate, 0.15 M NaCl, pH 7.4) by centrifugation at 3000 rpm for 10 min, and were then resuspended in PBS at a cell density of $5 \times 10^9$ SRBC/ml. To facilitate coupling of CTB to SRBC, SRBC were first coupled to GM1 ganglioside. A solution of PBS containing 300 nmol/ml GM1 ganglioside (Sigma Chemical Co., St Louis, Mo.) was added to packed SRBC at a ratio of 1:2 (vol/vol), and incubation was carried out at 37° C. for 2 hours in a shaking water bath. After 3 washes with PBS to remove excess GM1, GM1-coated red cells were resuspended in PBS to a density of $5 \times 10^9$ SRBC/ml and mixed with recombinant CTB (Sanchez, J., et al., *Proc. Natl. Acad. Sci. USA* 86:481–485, 1989) (final concentration 50 Fg/ml). After incubation for 2 hours at 37° C. in a shaking water bath to allow binding of CTB to GM1-coated SRBC, the red cell suspension was washed twice with PBS to remove non cell bound CTB, and resuspended in PBS. The final pellet was at a cell density of $1 \times 10^{10}$/ml.

To ascertain that the CTB molecules had bound to GM1-coupled SRBC and were still able to bind additional GM1 molecules, a solid phase hemadsorption assay using GM1 immobilized on plastic wells was employed. An aliquot of red cell suspension was diluted in PBS to a final concentration of 1% (packed vol/vol) supplemented with 0.1% (weight/vol) of bovine serum albumin (BSA) (Sigma) and added to GM1-coated U-shaped wells of plastic microtiter plates (Costar). After incubation at ambient (22° C.) temperature, wells were examined for appearence of hemadsorption. The specificity of the assay was established by the absence of hemadsorption in control wells that had not been coated with GM1, and by the dose-dependent inhibition of hemadsorptionby the addition of cell-free CTB to GM1-coated wells during incubation with the red blood cells.

Preparation of LTB-conjufated Sheep Red Blood Cells (SRBC-LTB)

GM1-coated SRBC ($5 \times 10^9$ GM1-SRBC/ml) were conjugated to recombinant LTB (50 Fg/ml) exactly as described above for coupling of SRBC to CTB.

Preparation of CTB-conjugated Human Gamma-globulins (HGG-CTB)

CTB and HGG were each coupled to N-succinimidyl (3-(2-pyridyl-dithio) propionate (SPDP) (Pharmacia, Uppsala, Sweden) (Carlsson, J., et al., *Biochem. J.* 173:723, 1978) at molar ratios of 1:5 and 1:10 respectively. SPDP was added to HGG and the mixture was allowed to incubate for 30 min at 23° C. with stirring. Excess SPDP was removed by gel filtration on a column of Sephadex G-25 (Pharmacia, Sweden) equilibrated with acetate buffer (0.1M sodium acetate, 0.1M NaCl, pH 4.5). The SPDP-derivatized HGG was reduced with dithiothreitol (DTT) (final concentration 50 mM) for 20 min at 23° C., and the resulting preparation was passed through a column of Sephadex G-25 equilibrated with phosphate-buffered saline (0.2M sodiumphosphate, NaCl 0.1 M, pH 8.5) to remove excess DTT and pyridine-2-thione released during reduction of SPDP-derivatized HGG.

CTB was diluted to 2 mg/ml in PBS and derivatized with SPDP as described above for HGG but at a molar ratio of 5:1 (SPDP:CTB). The resulting SPDP-derivatized CTB was passed through a column of Sephadex G-25 equilibrated in the same buffer, to remove excess unreacted SPDP.

SPDP-derivatized HGG and CTB were mixed at an equimolar ratio and incubated for 16 h at 23° C. The resulting CTB-HGG conjugate was purified by gel filtration through a column of Sephacryl S-300 to remove free CTB and/or HGG. The resulting conjugate was shown to contain $G_{M1}$ ganglioside binding capacity and to retain both CTB and HGG serological reactivities by means of an ELISA using $G_{M1}$ (Sigma, St Louis, Mo.) as solid phase capture system (Svennerholm, A.-M. et al. *Curr. Microbiol.* 1:19–23, 1978), and monoclonal and polyclonal antibodies to CTB and HGG as detection reagents (see below). Serial two-fold dilutions of the conjugate and of purified CTB- and HGG-SPDP derivatives were incubated in polystyrene wells that had previously been coated with GM1 ganglioside, and in wells coated with rabbit polyclonal IgG antibodies to HGG; next, horseradish peroxidase (HRP) conjugated rabbit ant-HGG or mouse monoclonal anti-CTB antibodies (appropriately diluted in PBS containing 0.05% Tween 20), followed by enzyme substrate, were applied sequentially to detect solid phase bound HGG and CTB. The amount of free and bound HGG and CTB was determined by reference to standard curves calibrated with known amounts of SPDP derivatized antigens. On average, the SPDP conjugation procedure and purification protocol described above yielded preparations containing negligible amounts of free HGG and less than 10% free CTB.

Immunization Protocols

Immunization with SRBC: Primary systemic immunization: Mice were injected in the rear left footpad with 40 Fl of pyrogen-free saline containing $10^7$ SRBC. Secondary systemic immunization: Five days after the primary immunization, mice were challenged by injecting the right rear footpad with 40 Fl of pyrogen-free saline containing $10^8$ SRBC.

Immunization with HGG: Prior to immunization, HGG was aggregated by heating at 63° C. for 30 min. Primary systemic immunization: Mice received 0.2 ml of aggregated HGG (500 Fg) emulsified in Freund's complete adjuvant (Difco, St Louis, Mo.) and administered by subcutaneous injections into the flanks. Secondary systemic immunization: Five days after the primary immunization, mice were challenged by injecting the right rear footpad with 40 Fl of pyrogen-free saline containing 1 mg of HGG.

Oral tolerance induction protocols: At various times before or after the primary systemic immunization with SRBC, mice were administered a single dose or daily consecutive doses of SRBC or SRBC-CTB. Each dose consisted of $2.5 \times 10^9$ SRBC or SRBC-CTB in 0.5 ml of PBS given by the intragastric route using a baby catheter feeding tube. Control animals were given 0.5 ml of PBS alone.

For induction of tolerance to HGG, mice were given a single oral dose of unconjugated HGG or CTB-conjugated HGG administered by intragastric tubing, 1 week before primary systemic immunization with HGG. Doses of 1 mg and 5 mg of unconjugated HGG and of 60 Fg of CTB-conjugated HGG were tested.

Evaluation of Delayed-type Hypersensitivity (DTH) Reactions

DTH to SRBC: Thickness of the right footpad was measured immediately before, and 2, 4, 24, and 48 h after the secondary systemic immunization with SRBC, using a dial gauge caliper (Oditest, H. C. Köplin, Schluchtem, Essen, Germany). The intensity of DTH reactions was determined for each individual animal by substracting the value obtained before challenge from those obtained at various times after challenge.

DTH to HGG: The intensity of DTH reactions to HGG injected in the right footpad was evaluated as above for SRBC.

Evaluation of Serum Antibody Responses

Serum anti-SRBC antibody responses: Immediately before the primary systemic immunization with SRBC administered in the left footpad, and 1–2 weeks after the secondary systemic immunization, a sample of blood was collected from the tail vein of individual mice and allowed to clot at room temperature for 60 min. Sera were heated at 56° C. for 45 min to inactivate complement, and then assayed for antibody levels to SRBC by direct and indirect hemagglutination assays. For direct hemagglutination, serial 2-fold dilutions of serum samples in PBS supplemented with 0.1% (weight/vol) of bovine serum albumin (PBS-BSA) were prepared in U-bottom wells of microtiter-plates. Fifty microliters of a suspension of 0.5% (packed vol/vol) SRBC in PBS-BSA were added to all wells and the plates were incubated for 1 hour at ambient temperature followed by an overnight incubation at 4° C. Wells were then examined for hemagglutination.

To detect non-hemagglutinating antibodies that had bound to SRBC, 25 Fl of PBS containing a mixture of heat-inactivated (56° C. for 45 min) rabbit antisera to mouse IgG and mouse IgA (final dilution 1:50) were added to wells corresponding to serum dilutions shown to be negative in the direct hemagglutination assay. The plates were then shaken to allow resuspension of SRBC and incubated undisturbed at 4° C. for 2 hours. Thereafter the wells were examined for hemagglutination. The reciprocal of the highest dilution of any given mouse serum causing hemagglutination of SRBC either directly or after addition of anti-mouse antisera (in the indirect hemagglutination assay) was determined and defined as the anti-SRBC antibody titer of said mouse serum.

Serum anti-HGG antibody responses: Serum IgM and IgG antibody levels to HGG were determined by standard solid phase ELISA using polystyrene microwells coated with HGG as solid phase capture system and HRP-conjugated affinity purified goat antibodies to mouse IgG and to mouse IgM (Southern Biotechnology Associates, Birmingham, Ala.) as detection reagents. Serial 5-fold dilutions of mouse sera were prepared in PBS containing 0.05% Tween 20 and incubated for 2 hrs at 23° C. in HGG-coated wells. After 5 washings with PBS containing 0.05% Tween 20, appropriately diluted HRP-antibodies to mouse IgM or IgG were added. Two hours later, plates were rinsed with PBS, and solid phase bound enzyme activity was revealed by addition of chromogen substrate, consisting of ABTS tablets (Southern Biotechnology Associates) dissolved in citrate-phosphate buffer, pH 5.0 and containing $H_2O_2$. Absorbance values were monitored 30 min later with an automated spectrophotometer (Titerscan, Flow Laboratories). The anti-HGG antibody titer of a mouse serum was defined as the reciprocal of the highest dilution given an absorbance value of at least twice that of control wells exposed to buffer alone instead of serum.

In vitro lymphocyte proliferation assay: Lymph nodes obtained 1–2 weeks after the secondary systemic immunization were minced in Iscove's medium (Gibco Europe, U.K.) and pressed through sterile nylon-mesh screens to yield single cell suspensions. The cells were washed twice and resuspended at $2\times10^6$ cells/ml in Iscove's medium supplemented with 5% heat-inactivated fetal bovine serum (FBS), L-glutamine (1%), sodium pyruvate (1%), non-essential aminoacids (1%), 2-mercaptoethanol ($5\times10^{-5}$ M) and gentamycin (20 Fg/ml). Lymph node cells were added to flat-bottom microtiterwells (Nunc, Denmark) containing a previously titrated amount of SRBC in a total volume of 200 Fl. The plates were then incubated at 37° C. in 5% $CO_2$ in air for 3 days. The cultures were pulsed during the last 16 hrs with $^3$H-thymidine (2.0 mCi/mM, Amersham, Stockholm), individual wells were harvested using a 96-well automated cell-harvester (Inotech, Basel, Switzerland) and the radio-nucleotide incorporation was measured with an argon-activated scintil-lation counter (Inotech).

The level of $^3$H-thymidine incorporation was calculated as the stimulation index (S.I.)=CPM of lymph node cells+SRBC/CPM of lymph node cells alone.

EXAMPLE 1

Prevention of Early and Late Delayed-type Hypersensitivity DTH Reactions by Oral Administration of Sheep Red Blood Cells (SRBC) Linked to the B Subunit of Cholera Toxin (CTB)

Mice were fed a single dose of SRBC-CTB, SRBC alone, or saline 1 to 8 weeks before aprimary systemic immunization with SRBC injected inthe left rear footpad. Five days after this injection, the right rear footpad was challenged so as to elicit a DTH reaction. The results are tabulated in Table 2.

TABLE 2

| feeding | number of feedings | mean footpad thickness increment x $10^{-3}$ cm (±1 standard deviation) | | |
|---|---|---|---|---|
| | | 4 hrs | 24 hrs | 48 hrs |
| SRBC-CTB | 1 | 11 ± 2.0* | 23 ± 12.1** | 16 ± 4.6* |
| SRBC | 1 | 45 ± 4.2 | 50 ± 10.6 | 30 ± 4.6 |
| SRBC | 5 | 34 ± 9.1 | 59 ± 6.0 | 34 ± 6.1 |
| SRBC | 10 | 34 ± 7.6 | 41 ± 3.8 | 29 ± 8.6 |
| SRBC | 15 | 32 ± 7.4 | 33 ± 8.1* | 24 ± 6.3 |
| SRBC | 20 | 31 ± 13.0 | 25 ± 5.5** | 16 ± 4.4* |
| saline | | 35 ± 10.8 | 50 ± 12.7 | 32 ± 8.3 |

Asterisks denote significant differences between values determined on test groups (6 animals per group) and on control group consisting of animals (7 mice) fed saline only:
*, $p < 0.05$ and ** $p < 0.01$ (Student's test).

The intensity of DTH reactions elicited in mice fed SRBC alone was comparable to that recorded in control mice fed saline only. By contrast, DTH reactions recorded in mice fed SRBC conjugated to the mucosa-binding molecule CTB were considerably decreased at all times recorded. Thus, two hours after challenge with SRBC (that is, at a time corresponding to the early peak of DTH responses seen in control animals), footpad swelling was absent in mice previously fed a single dose of SRBC-CTB. Furthermore, the late DTH response (which, in mice, peaks at 24 hours postchallenge) was significantly decreased as compared to control animals (animals fed saline or SRBC alone).

In a second set of experiments, mice were fed single or daily consecutive doses of SRBC-CTB or SRBC. One week after the last oral administration, animals were primed and challenged as above by systemic injections of SRBC in the left footpad, followed 5 days later by the right footpad. The results are shown in Table 3.

TABLE 3

| systemic sensitization with SRBC (day 0) | feeding (day 4) 1 dose of: | mean footpad thickness increment x $10^{-3}$ cm ("1 standard deviation") after systemic challenge with SRBC (day 7) | | |
|---|---|---|---|---|
| | | 4 hrs | 24 hrs | 48 hrs |
| + | SRBC-CTB | 23 ± 33** | 20 ± 7.1** | 12 ± 3.8* |
| + | SRBC | 50 ± 8.2 | 44 ± 7.4 | 28 ± 5.4 |
| + | saline | 61 ± 7.4 | 53 ± 4.7 | 25 ± 6.2 |
| − | saline | 28 ± 1.0 | 29 ± 0.5 | 12 ± 3.5 |

Asterisks denote significant differences between values determined on test groups (6 animals per group) and on control group (6 mice) consisting of animals sensitized with SRBC buffed saline only before challenge
* $p < 0.05$ and ** $p < 0.01$ (Student's test).

It was found that the daily oral administration of SRBC for 3–4 weeks was required to suppress the 24-hr DTH reactions to a level comparable to that achieved by a single administration of SRBC-CTB. It should be pointed out, however, that as many as 20 consecutive feedings with SRBC over a 4 week period had no effect on the development of the early phase (2–4 hours) of the DTH response, in contrast to the situation seen with animals fed a single dose of SRBC conjugated to CTB, who failed to develop an early DTH response.

EXAMPLE 2
Inhibition of Early and Late DTH Reactions by Oral Administration of Sheep Red Blood Cells (SRBC) Linked to the B Subunit of Cholera Toxin (CTB) in Immune Mice To determine whether mucosal administration of CTB-conjugated antigens would suppress DTH reactions in animals previously systemically sensitized to the same antigen, SRBC were first injected in the left rear footpad of mice to induce a state of primary systemic immunity. Four days later, animals were fed a single oral dose of SRBC-CTB, SRBC alone, or saline. Two days after the latter feeding, animals were given a second injection of SRBC in the right footpad to elicit DTH reactions. The latter DTH responses were monitored at various times after this secondary systemic immunization. Whereas mice fed SRBC alone developed DTH responses undistinguishable from those seen in control animals fed only saline, mice fed SRBC-CTB had considerably reduced early and late DTH responses to SRBC. Therefore, it appears that oral administration of SRBC-CTB can induce suppression of both early and late DTH responses to systemically injected SRBC even in animals previously sensitized (primed) systemically to SRBC.

EXAMPLE 3
Inhibition of Lymphocyte Proliferation by Oral Administration of Sheep Red Blood Cells (SRBC) Linked to the B Subunit of Cholera Toxin (CTB)

To determine whether oral administration of CTB-conjugated antigens would result in decreased proliferative responses of lymph node cells to said antigens, mice were fed a single dose of CTB-conjugated SRBC and were then injected in the left footpad with SRBC (primary systemic in vivo immunization). One week later, the ability of lymph node cells to proliferate after in vitro exposure to the homologous antigen (SRBC) was examined. The results are shown in Table 4.

TABLE 4

| feeding one dose of: | mean S. I. values " standard deviation in cultures exposed to | |
|---|---|---|
| | SRBC | concanavalin A |
| SRBC-CTB (n = 6 mice) | 1.06 ± 0.29* | 119 ± 32 |
| SRBC (n = 6 mice) | 7.88 ± 4.52 | 108 ± 56 |
| saline (n = 6 mice) | 8.94 ± 3.89 | 76 ± 35 |

* denotes significant difference ($P < 0.01$; Student't test) between test SRBC-CTB fed animals and animals fed SRBC alone or fed saline only.

Compared to control animals fed saline only, and animals fed a single dose of SRBC alone, lymph node cells from animals fed SRBC-CTB had decreased proliferative responses when cultured with SRBC. This decrease was specific for the antigen administered, inasmuch as the proliferative responses of lymph node cells to the mitogen concanavalin A were comparable in animals fed SRBC-CTB, SRBC or saline only.

EXAMPLE 4
Inhibition of Early and Late DTH Reactions by Oral Administration of Sheep Red Blood Cells (SRBC) Linked to the B Subunit of Escherichia Coli Heat-labile Enterotoxin B Subunit (LTB)

To determine whether mucosal administration of SRBC conjugated to another mucosa-binding molecule, the B subunit of *Escherichia coli* heat-labile enterotoxin B subunit (LTB), would also suppress DTH reactions to systemically administered SRBC, mice were fed a single dose of SRBC-LTB or saline, which was given 1 week before a primary footpad injection with SRBC. For comparative purposes, an additional group of mice was fed with SRBC-CTB. Five days after the primary injection, all mice were challenged with SRBC in the contralateral footpad so as to elicit a DTH reaction. The results are shown in Table 5.

TABLE 5

| feeding | mean footpad thickness increment x $10^{-3}$ cm (±1 standard deviation) | | | |
|---|---|---|---|---|
| | 2 hrs | 4 hrs | 24 hrs | 48 hrs |
| SRBC-LTB | 4 ± 10 | 16 ± 8.2 | 38 ± 12* | 13 ± 2.2* |
| SRBC-CTB | 0 ± 0* | 6 ± 5.4* | 22 ± 6.7* | 7.1 ± 3** |
| saline | 7 ± 5.5 | 14 ± 2.3 | 50 ± 4.3 | 24 ± 3.5 |

Asterisks denote significant differences between test groups (7 mice per group) and control animals (n = 6 mice) fed saline only: * $p < 0.05$ and ** $p < 0.01$ (Student't test).

At 24 hr post-challenge, DTH reactions recorded in mice fed SRBC-LTB were significantly reduced as compared to saline fed control mice. However, the early (2–4 hrs) DTH reactions were not reduced in mice fed SRBC-LTB. This contrasted with DTH reactions recorded in mice fed SRBC-CTB, which were absent at 2–4 hrs post-challenge and were significantly reduced at 24–48 hrs. These observations indicate that oral administration of SRBC conjugated to LTB can induce suppression of the late DTH response to systemically injected SRBC but does not affect the early component of such responses.

EXAMPLE 5
Inhibition of Early and Late Delayed-type Hypersensitivity (DTH) Reactions to Human Gamma Globulins (HGG) by Oral Administration of HGG Conjugated to the B Subunit of Cholera Toxin (CTB)

To determine whether mucosal administration of CTB-conjugated antigens would suppress DTH reactions to a soluble protein antigen, mice were fed a single dose of HGG conjugated to CTB, HGG alone, or saline. These were given to separate groups of mice 1 week before a primary systemic immunization with HGG in Freund's complete adjuvant injected subcutaneously. Five days after this injection, the right rear footpad was challenged with HGG so as to elicit a DTH reaction. The intensity of DTH reactions elicited in mice fed 1 mg of HGG alone was comparable to that in control mice fed saline only, at all times examined after challenge. The results are shown in Table 6.

TABLE 6

| Group | Feeding | Sensitization$ | \multicolumn{4}{c}{mean footpad thickness increment × $10^{-3}$ cm after systematic challenge with HGG¶} | | | |
|---|---|---|---|---|---|---|
| | | | 2 hrs | 4 hrs | 24 hrs | 48 hrs |
| I | HGG(66Fg)-CTB | + | 18 ± 5.1* | 45 ± 7* | 30 ± 6.2** | 26 ± 4.5* |
| II | HGG(15Fg)-CTB | + | 38 ± 8.4 | 68 ± 7.1 | 34 ± 3.2** | 27 ± 4.4* |
| III | HGG 5 mg | + | 40 ± 7.6 | 51 ± 13 | 37 ± 5** | 28 ± 1.9* |
| IV | HGG 11 mg | + | 38 ± 5.5 | 57 ± 17 | 45 ± 7.4 | 36 ± 6.8 |
| V | saline | + | 39 ± 8.7 | 59 ± 5.8 | 51 ± 2.9 | 39 ± 12 |
| VI | saline | − | 23 ± 5.7 | 43 ± 18 | 22 ± 8 | 17 ± 2.5 |

$Animals were sensitized by subcutaneous injection of 0.5 mg heat-aggregated HGG in Freund's complete adjuvant.
¶Animals were challenged by injecting the right footpad with 1 mg HGG in saline.
Asterisks denote significant differences between test groups (group I–IV, n = 6 mice per group) and control animals fed saline only (group V, n = 6 mice): *p < 0.05 and **p < 0.01 (Student's test).

Feeding mice 5 mg of HGG resulted in decreased DTH reactions at 24–48 hrs but did not influence the intensity of the early (2–4 hrs) phase of these reactions. In contrast, DTH reactions monitored in mice fed as little as 15 Fg of HGG conjugated to CTB, that is a more than 300-fold lower amount of HGG, had similar effects, being significantly lower than corresponding reactions in control (saline fed) animals at 24 hrs, but not at earlier times (2 and 4 hrs). However, feeding mice with 66 Fg of HGG conjugated to CTB resulted in considerably decreased DTH reactions at all times recorded. Thus, the early (2–4 hr) and late (24–48 hr) DTH reactions were virtually abrogated in mice fed 66 Fg of HGG conjugated to CTB. These observations demonstrate that oral administration of small amounts of a soluble protein antigen conjugated to the mucosa-binding molecule CTB can induce suppression of both early and late DTH reactions to subsequent systemic injection with said protein antigen.

EXAMPLE 6

Abrogation of CTB-induced Tolerance by Intact Cholera Toxin

Mice were fed a single dose of SRBC conjugated to intact cholera toxin (CT) instead of to CTB. Alternatively, mice were fed free CT or (as a control) free CTB together with CT-SRBCs. One week later, a primary systemic immunization with SRBC was injected in the left rear footpad. Five days after this injection, the right rear footpad was challenged so as to elicit a DTH reaction. The results are shown in Table 7.

TABLE 7

| | | \multicolumn{2}{c}{Specific thickness increment†, cm × $10^3$ (% inhibition)} | |
|---|---|---|---|
| Exp. | Feeding* | 2 hr | 24 hr |
| 1 | CTB-SRBCs | −4 ± 4.5 (156:P < 0.01) | 5 ± 2.4 (87:P < 0.01) |
| | CT-SRBCs | 21 ± 4.1 (−133) | 50 ± 5.6 (1−28) |
| | Saline | 9 ± 1.5 | 40 ± 2.9 |
| 2 | CTB-SRBCs | −3 ± 2.0 (113:P < 0.01) | 14 ± .5 (68:P < 0.01) |
| | CTB-SRBCs + 10 ng of CT | 20 ± 3.9 (−18) | 57 ± 7.8 (−30) |

TABLE 7-continued

| | | \multicolumn{2}{c}{Specific thickness increment†, cm × $10^3$ (% inhibition)} | |
|---|---|---|---|
| Exp. | Feeding* | 2 hr | 24 hr |
| | CTB-SRBCs + 10 Fg of CTB | −3 ± 3.1 (113:P < 0.01) | 19 ± 8.2 (57:P < 0.01) |
| | CTB-SRBCs + 500 Fg of CTB | 0 ± 4.0 (100:P < 0.01) | 11 ± 4.0 (75:P < 0.01) |
| | Saline | 17 ± 4.2 | 44 ± 6.5 |

*Mice were fed single doses of CTB-conjugated SRBCs with or without free CT or CTB, given 7 days prior to systemic priming with SRBCs.
†Mean(+SD) determined on groups of six to eight mice challenged 7 days after systemic priming. Where significant, differences between experimental and saline-fed control animals are indicated (Wilcoxon rank test).

Feeding mice one dose of SRBC-CT not only failed to suppress early and later DTH responses to SRBCs but was in fact effective at priming animals for systemic DTH responses to SRBCs. Mice fed free CT together with CTB-SRBCs developed normal if not enhanced DTH and serum antibody responses to SRBCs compared to mice fed SRBC-CTB alone. By contrast, feeding mice as much as 500 Fg of free CTB together with CTB-SRBCs had no effect on suppression of DTH reactivity to SRBCs.

We claim:

1. An immunological tolerance-inducing agent comprising a mucosa-binding molecule linked to a specific antigen derived from an infectious microorganism, wherein said mucosa binding molecule is selected from mucosa binding molecules selected from the group consisting of pure cholera toxin B subunit, pure *Escherichia coli* heat-labile enterotoxin B subunit, and mucosa-binding fragments thereof and wherein infection of a host with said microorganism causes an unwanted immune response in said host.

2. An agent as defined in claim 1, wherein said unwanted immune response comprises delayed-type hypersensitivity (DTH).

3. An agent as defined in claim 2, wherein said antigen comprises a DTH epitope.

4. An agent as defined in claim 1, wherein said unwanted immune response is associated with systemic production of IgM and IgG antibodies specific to said antigen.

5. An agent as defined in claim 1, wherein said antigen is selected from the group consisting of peptides and proteins.

6. An agent as defined in claim 5, wherein said protein is a heat shock protein.

7. An agent as defined in claim 1, wherein said mucosa-binding molecule is directly linked to said specific antigen.

8. An agent as defined in claim 7, wherein said direct linkage is selected from the group consisting of covalent and non-covalent linkages.

9. An agent as defmed in claim 8, wherein said linkage comprises a peptide bond.

10. An agent as defined in claim 1, wherein said mucosa-binding molecule is indirectly linked to said specific antigen.

11. An agent as defined in claim 10, wherein said indirect linkage is selected from the group consisting of covalent and non-covalent linkages.

12. An agent as defined in claim 10, wherein said linkage is achieved using a protective vehicle containing said antigen.

13. An agent as defined in claim 10, wherein said linkage is achieved using a spacer molecule.

14. An agent as defined in claim 13, wherein said spacer molecule specifically binds said antigen, said mucosa-binding molecule, or both.

15. An agent as defined in claim 14, wherein said spacer molecule comprises an antibody.

16. An agent as defined in claim 14, wherein said spacer molecule comprises galactosyl-N-acetylgalactosaminyl-(sialyl)-galactosylglucosylceramide.

* * * * *